US 6,598,235 B2

(12) United States Patent
Bulla

(10) Patent No.: US 6,598,235 B2
(45) Date of Patent: Jul. 29, 2003

(54) GARMENT, UNDERGARMENT OR GARMENT LINER ACCOMMODATING A HEATING DEVICE

(76) Inventor: Athalene April Bulla, 47 Broadway Ave., Sayville, NY (US) 11782

( * ) Notice: Subject to any disclaimer, the term of this patent is extended or adjusted under 35 U.S.C. 154(b) by 0 days.

(21) Appl. No.: 09/921,284

(22) Filed: Aug. 2, 2001

(65) Prior Publication Data

US 2002/0062509 A1 May 30, 2002

Related U.S. Application Data

(60) Provisional application No. 60/222,486, filed on Aug. 2, 2000.

(51) Int. Cl.$^7$ ................................................ A41B 1/00
(52) U.S. Cl. ................................................ 2/69; 2/115
(58) Field of Search ........................ 2/16, 20, 22, 59, 2/60, 62, 69, 73, 94, 102, 125, 158, 159, 160, 311, 912; 54/82; 119/850; 126/204; 128/869, 878; 601/15

(56) References Cited

U.S. PATENT DOCUMENTS

| 4,527,566 | A | * | 7/1985 | Abare ........................ 601/15 |
| 4,535,482 | A | * | 8/1985 | Spector et al. ................ 2/160 |
| 4,971,041 | A | * | 11/1990 | Millikan et al. ............. 128/878 |
| 4,985,934 | A | * | 1/1991 | Perry ............................ 2/125 |
| 5,152,285 | A | * | 10/1992 | Gnegy ........................... 54/82 |
| 5,290,218 | A | * | 3/1994 | Kilbey ........................ 128/869 |
| 5,496,358 | A | * | 3/1996 | Rosenwald ................. 126/204 |
| 5,605,144 | A | * | 2/1997 | Simmons et al. ........... 126/204 |
| 5,665,057 | A | * | 9/1997 | Murphy ........................ 2/311 |
| 5,826,273 | A | * | 10/1998 | Eckes ........................... 2/115 |
| 5,873,903 | A | * | 2/1999 | Garcia .......................... 2/912 |
| 6,029,277 | A | * | 2/2000 | Picchione, II .................. 2/16 |
| 6,240,882 | B1 | * | 6/2001 | Gross ......................... 119/850 |

* cited by examiner

Primary Examiner—Gary L Welch
(74) Attorney, Agent, or Firm—Michelle Carniaux

(57) ABSTRACT

A device for applying heat from a heating device to appendage of a wearer is described. The device includes a base layer including a pocket. The base layer is configured to accommodate the appendage of the wearer. The pocket is configured for removable insertion of the heating device so that when the heating device is inserted in the pocket and the device is worn by the wearer, heat from the heating device is applied to the appendage.

28 Claims, 20 Drawing Sheets

5a  5b

6a

6b

Front side of the body

Backside of the body

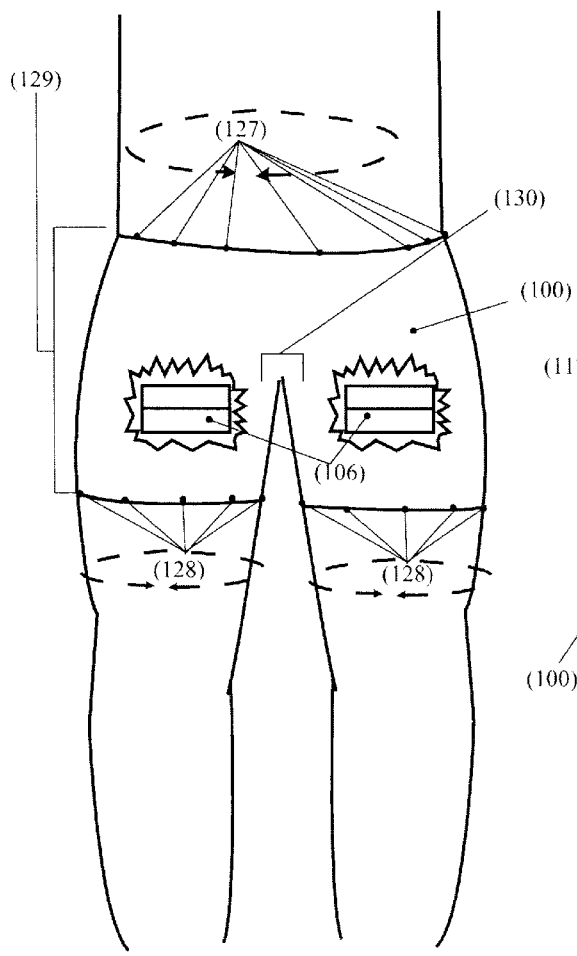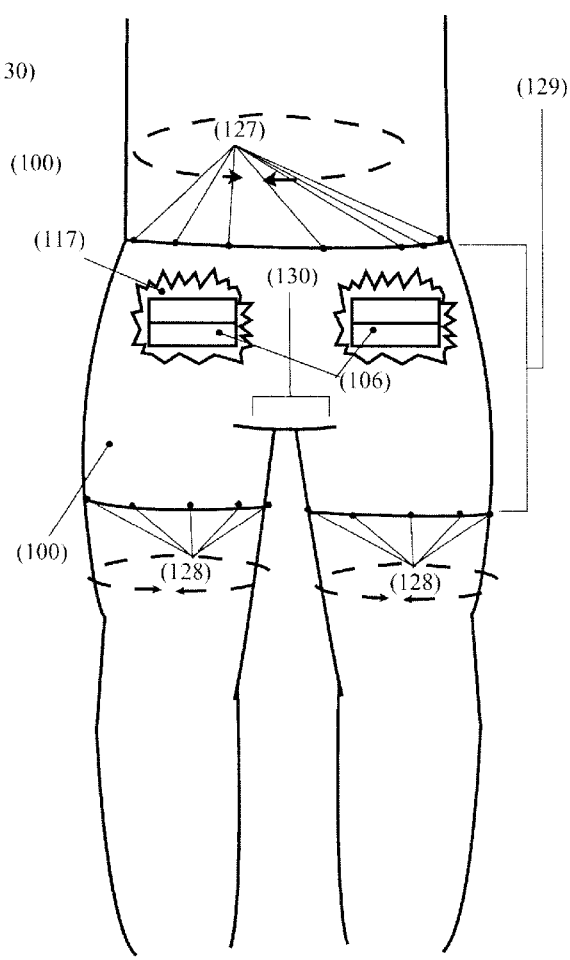

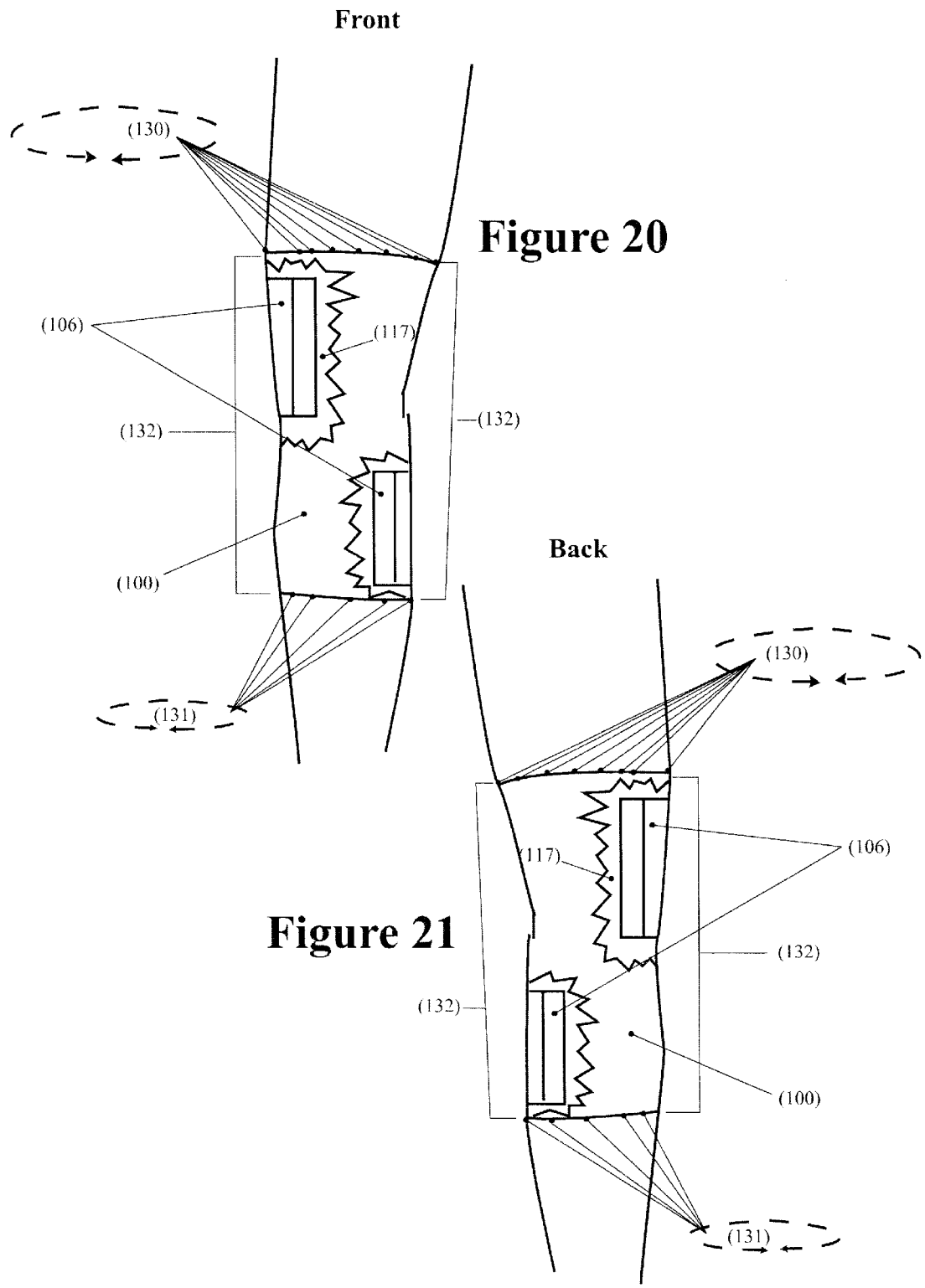

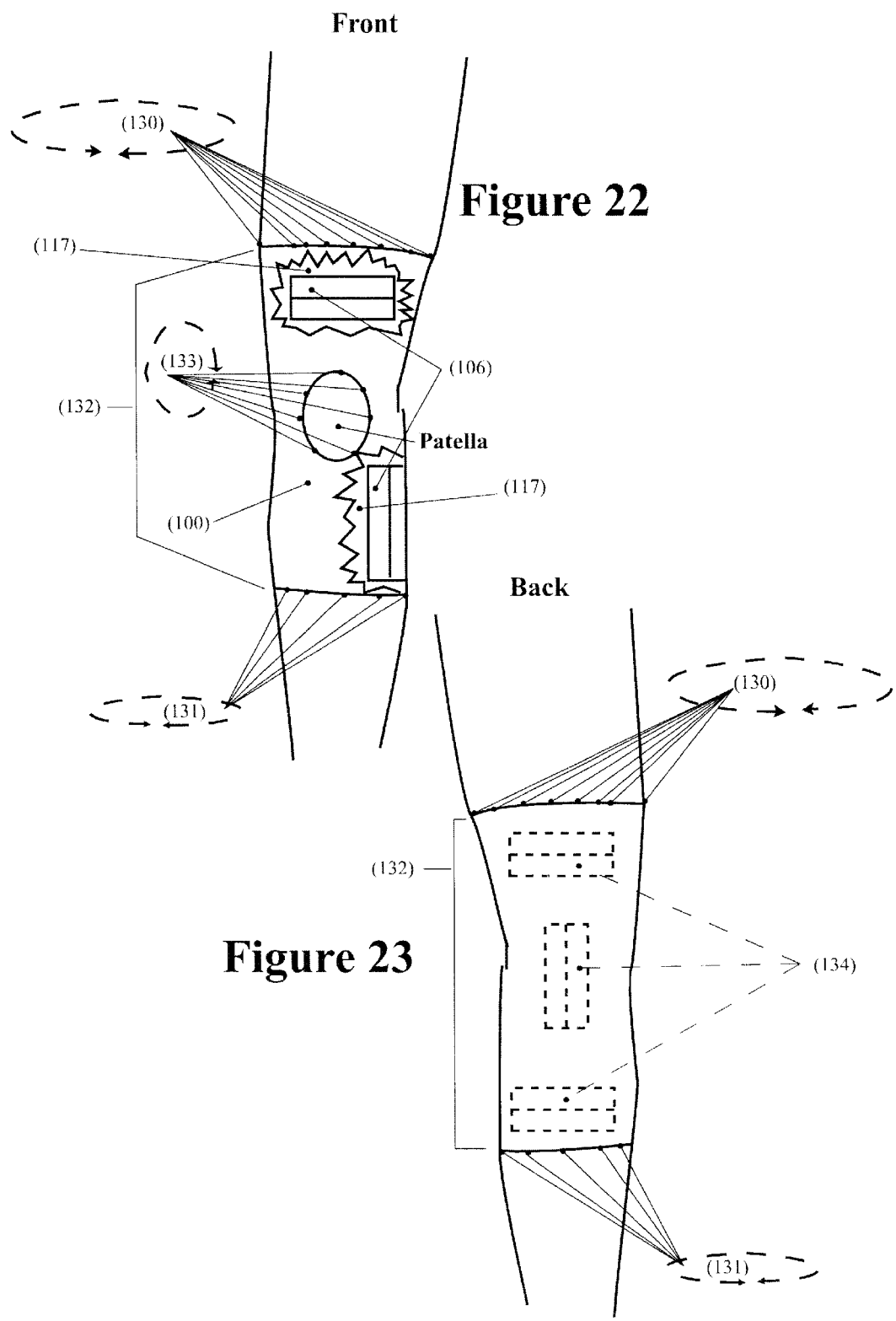

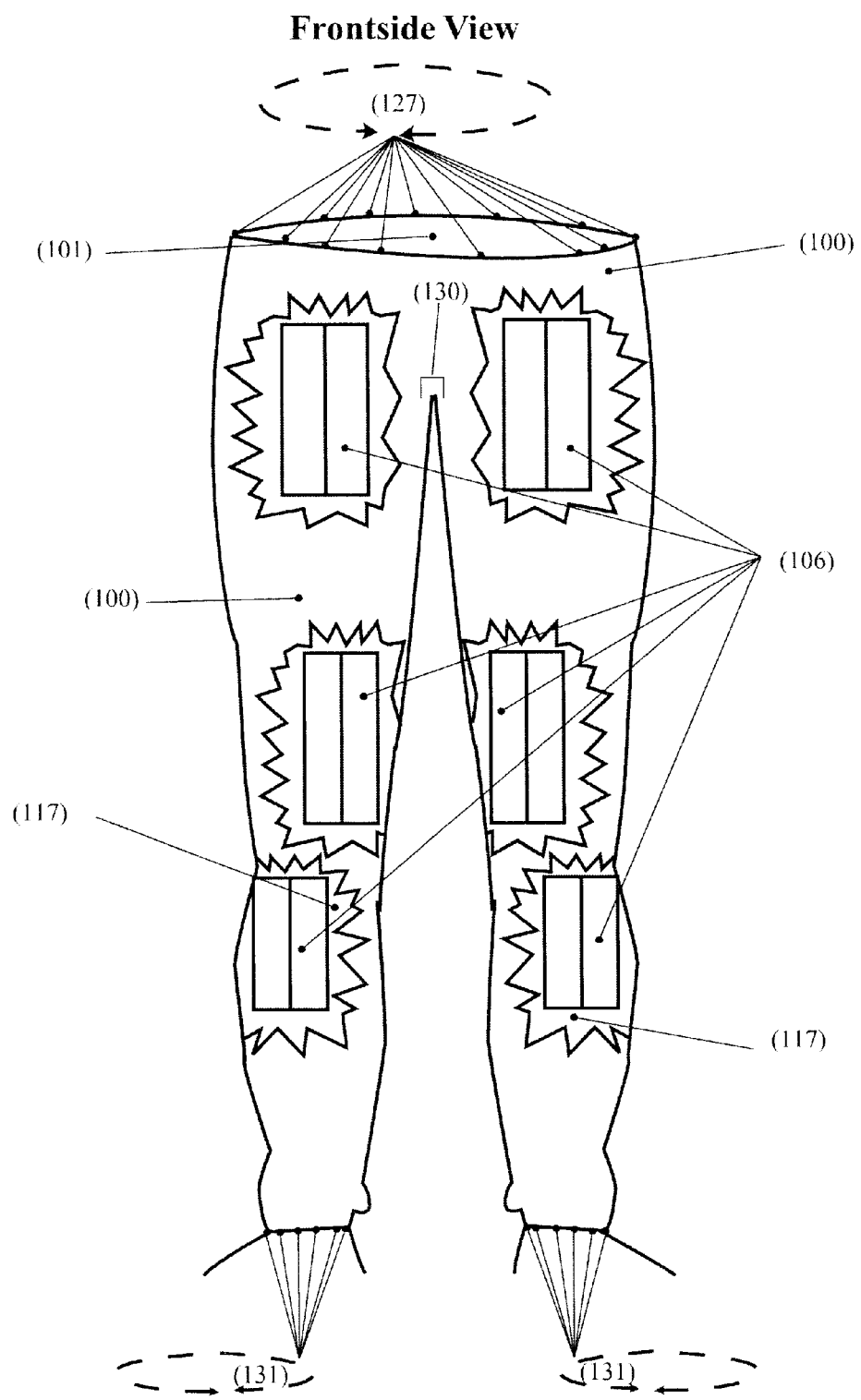

Lateral View

Medial View

Frontal View

US 6,598,235 B2

GARMENT, UNDERGARMENT OR GARMENT LINER ACCOMMODATING A HEATING DEVICE

CROSS REFERENCE

This application claims the benefit under 35 U.S.C. §119 (e) of U.S. patent application Ser. No. 60/222,486 filed on Aug. 2, 2000, which is expressly incorporated herein by reference in its entirety.

FIELD OF THE INVENTION

The present invention relates to a garment used for enabling the supply of heat to an appendage of a body.

BACKGROUND INFORMATION

There are various portable heat emitting devices on the product market for the purpose of maintaining or providing extra warmth to a body. For example, electrically heated socks are available which may be worn on the feet of a wearer. Also, air-activated heat packs are available which may be inserted into gloves, in a jacket pocket, or placed in footwear.

SUMMARY

In accordance with example embodiments of the present invention, a device for applying heat from a heating device to appendage of a wearer is described. The device includes a base layer including a pocket. The base layer is configured to accommodate the appendage of the wearer. The pocket is configured for removable insertion of the heating device so that when the heating device is inserted in the pocket and the device is worn by the wearer, heat from the heating device is applied to the appendage. The device may be, for example, a garment, undergarment or garment liner.

BRIEF DESCRIPTION OF THE DRAWINGS

FIG. 18 shows a front view of a warmer for the lower torso or lower trunk of a wearer, according to one example embodiment of the present invention.

FIG. 19 shows a rear view of the warmer of FIG. 18.

FIG. 20 shows a front view of a warmer for an area around the knee of the wearer, according to one example embodiment of the present invention.

FIG. 21 shows a rear view of the warmer of FIG. 20.

FIG. 22 shows a front view of a wanner for an area around the knee of the wearer, according to another example embodiment of the present invention.

FIG. 23 shows a rear view of the warmer of FIG. 22.

FIG. 24 shows a front view of a warmer for the legs of the wearer, according to one example embodiment of the present invention.

DETAILED DESCRIPTION

Figure 1:
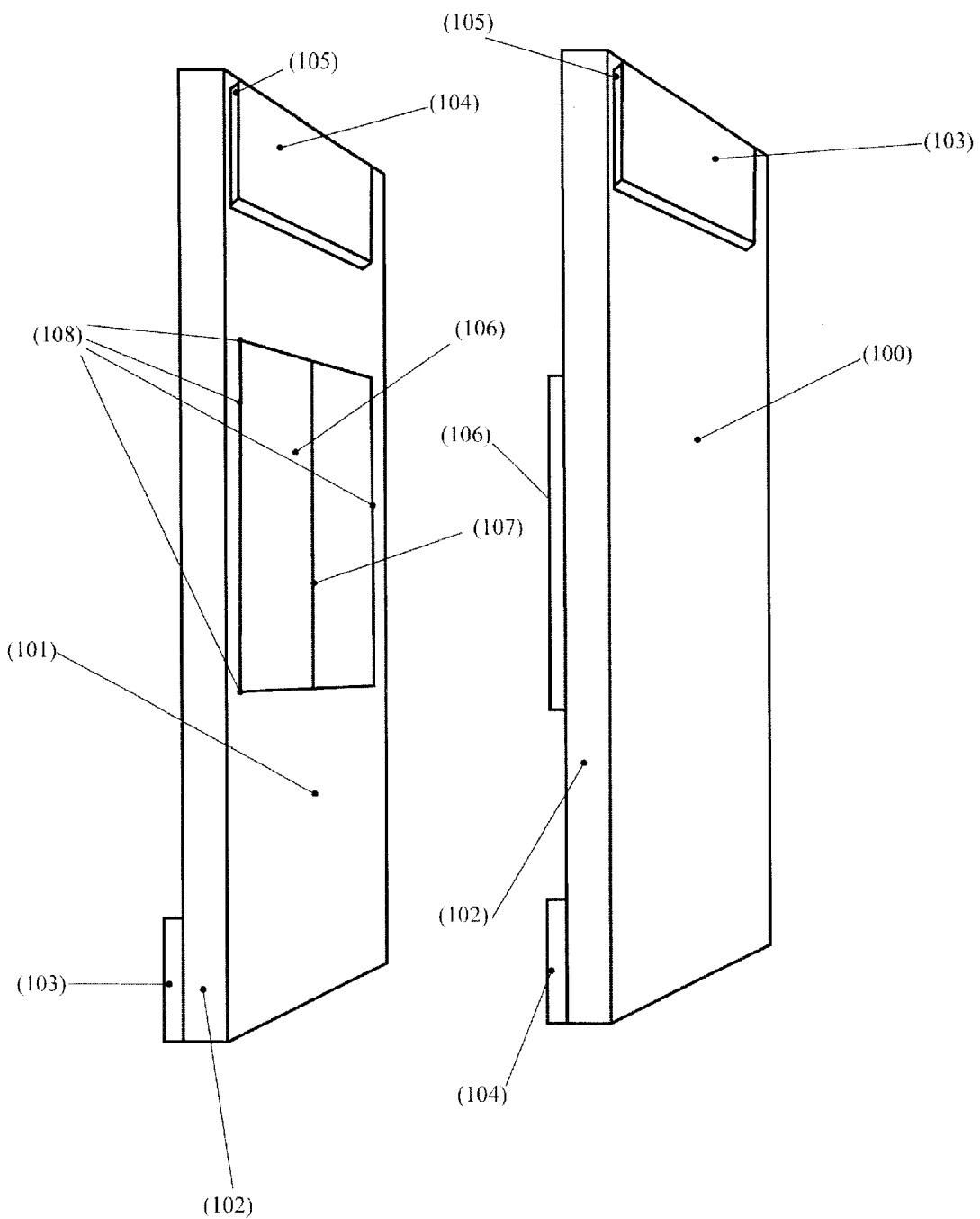
FIG. 1 shows two views of a wrist wrap in accordance with one example embodiment of the present invention.

FIG. 1 shows two views of one example embodiment of the present invention. In accordance with this embodiment of the present invention, a wrist wrap is provided. The example wrist wrap includes a base layer 100, 101, 102. The base layer 100, 101, 102 maybe composed of any flexible material or textile including, for example, neoprene, spandex, cotton fabric, nylon, lycra, latex, rubber, etc. The base layer 100, 101, 102 is sized accommodate the wrist of a person or animal.

The base layer 100, 101, 102 includes a pocket 106. In the example embodiment, the pocket 106 includes an opening 107 on the interior side 101 of the base layer, e.g., the side of the base layer that, when worn, is proximal to the wearer. In an alternative embodiment of the present invention, the pocket 106 may open to the exterior side of the base layer, e.g., the side of the base layer that, when worn, is distal to the wearer.

Attached to the ends of the base layer 100, 101, 102 are fasteners 103, 104. In the example embodiment, the fasteners 103, 104 are hook and loop type fasteners, such as, for example, VELCRO fasteners. However, other types of fasteners such as snaps, buttons, seams, and zippers, may, of course, be used. The fasteners may also include material such as fabric, string, yarn, etc. that can be tied together. In this example embodiment, the base layer 100, 101, 102 may be wrapped around the wrist of a wearer, and fastened in place using the fasteners 103, 104.

The pocket 106 is formed of a flexible material such as cotton/lycra, fleece, etc. In the example embodiment, the pocket is formed by two overlapping pieces of material 108, which are connected to the base layer 100, 101, 102. In an alternative embodiment of the present invention, the pocket may be formed by two non-overlapping pieces of material 108, which are connected to the base layer 100, 101, 102. In another embodiment of the present invention, the pocket may be formed slitting a single piece of material, and connecting the slitted material to the base layer 100, 101, 102. In yet another embodiment of the present invention, the pocket is integral with the base layer 100, 101, 102. For example, the base layer may include a number of sublayers, the inner most sublayer (i.e., the sublayer proximal to the wearer) having a slit.

In accordance with the example embodiment of the present invention, the pocket 106 receives a heating device such as an air activated heat pack. The heat pack may be composed of, for example, iron or iron powder, (iron oxide, when activated), water, salt, activated charcoal and vermiculite. The heating device may be removably inserted into the pocket 106. That is, the heating device may be inserted into the pocket 106 and removed from the pocket 106.

Figure 1A:
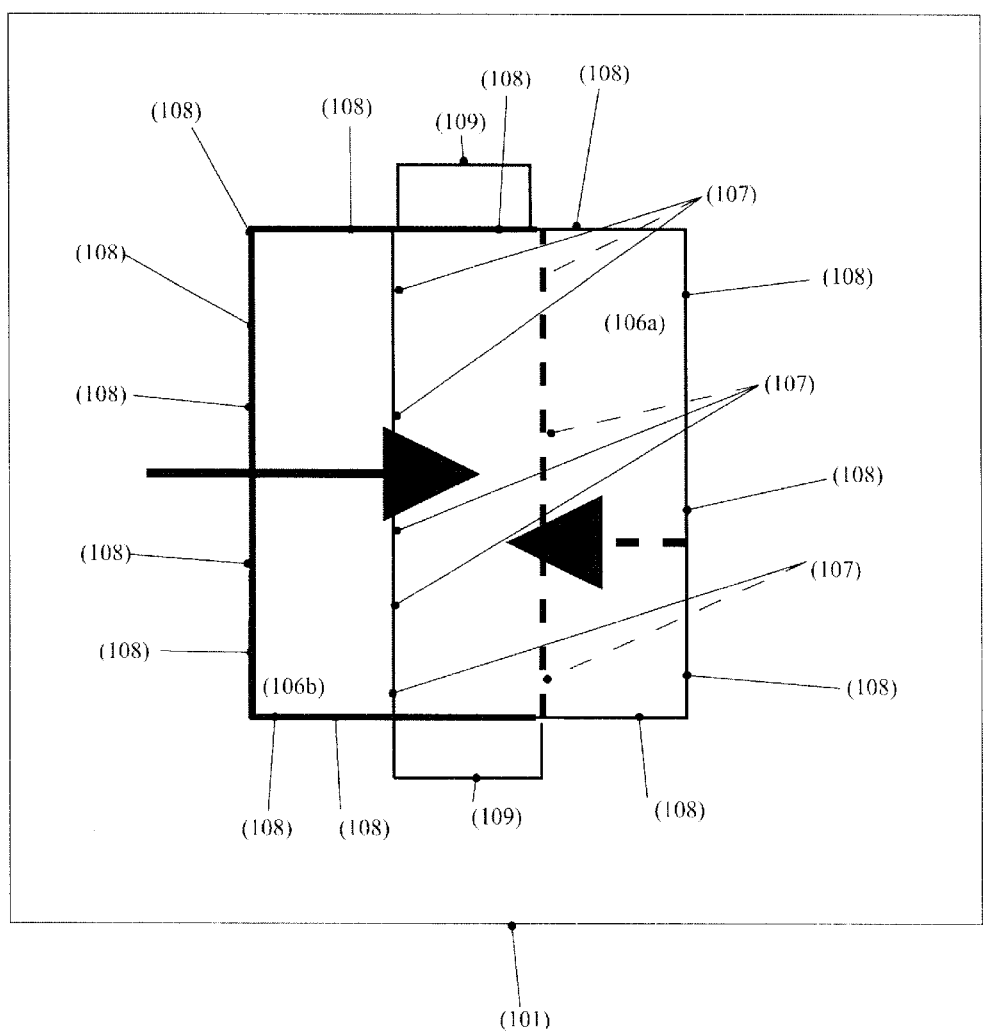
FIG. 1a shows an example of a pocket according to one example embodiment of the present invention.

FIG. 1a shows one example embodiment of a pocket. In this embodiment, the pocket may include two overlapping flaps of material 108. These two overlapping flaps 108 may or may not be of the same dimension. In the example embodiment of FIG. 1a, the flaps are of the same dimension. Here, a first one of the flaps 106a is placed on top of the other flap 106b, so that an overlap portion 109 is formed. Outer edges of the flaps 106a, 106b are connected to the base layer. In this embodiment, the inner edges 107 of the flaps 106a, 106b are free so that a heating device may be inserted into the pocket.

Figure 2:
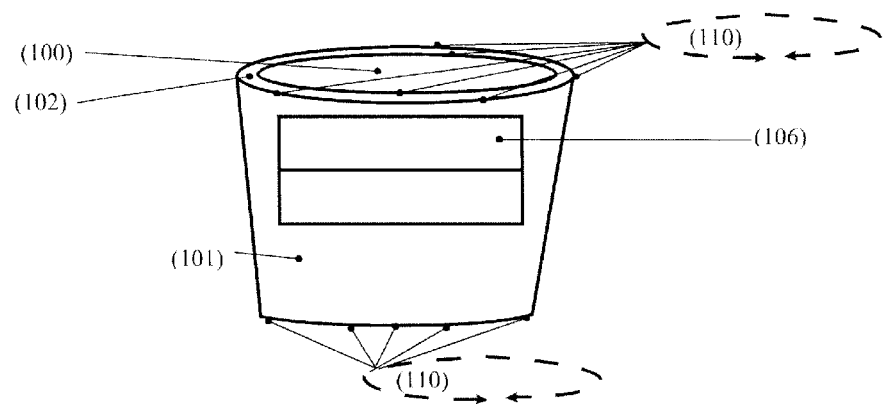
FIG. 2 shows a wrist cuff (inside-out) in accordance with one example embodiment of the present invention.

FIG. 2 shows another example embodiment of the present invention. This example embodiment is similar to the embodiment of FIG. 1, except that the base layer is formed of a continuous strip of material (which may or may not have seams, depending on the composition of the base layer and the manufacturing techniques used). In this example, the base layer forms a "cuff," e.g., a wrist cuff, of elastic material and is configured to slip over the hand and onto the wrist of a wearer. As shown in FIG. 2, the wearer's hand is inserted into 110. This figure shows the cuff flipped inside-out to show the pocket 106.

Figure 3:
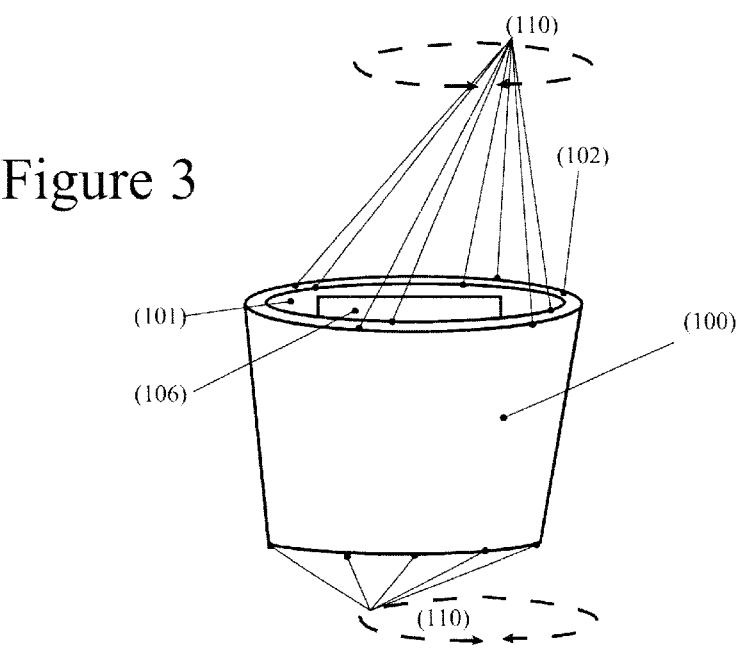
FIG. 3 shows the wrist cuff of FIG. 2, right-side out.
Figure 4:
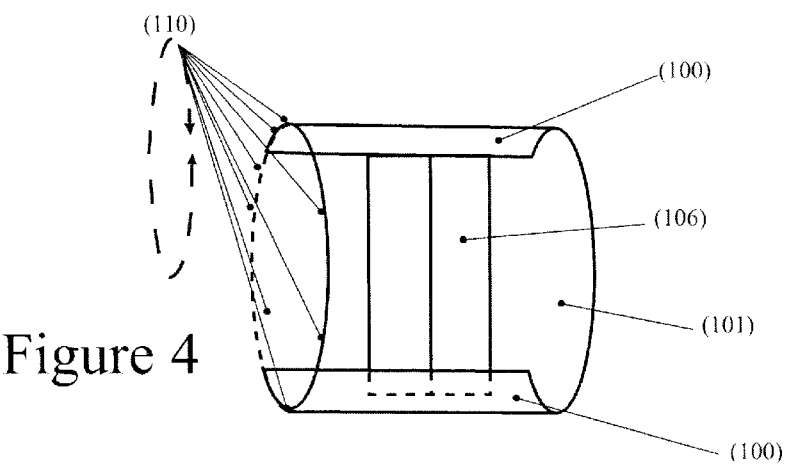
FIG. 4 shows a sectional view of the wrist cuff of FIGS. 2 and 3.

FIG. 3 shows the example embodiment shown in FIG. 2, right-side out. FIG. 4 shows a sectional view of the wrist cuff of FIGS. 2 and 3.

Figures 5A, 5B:
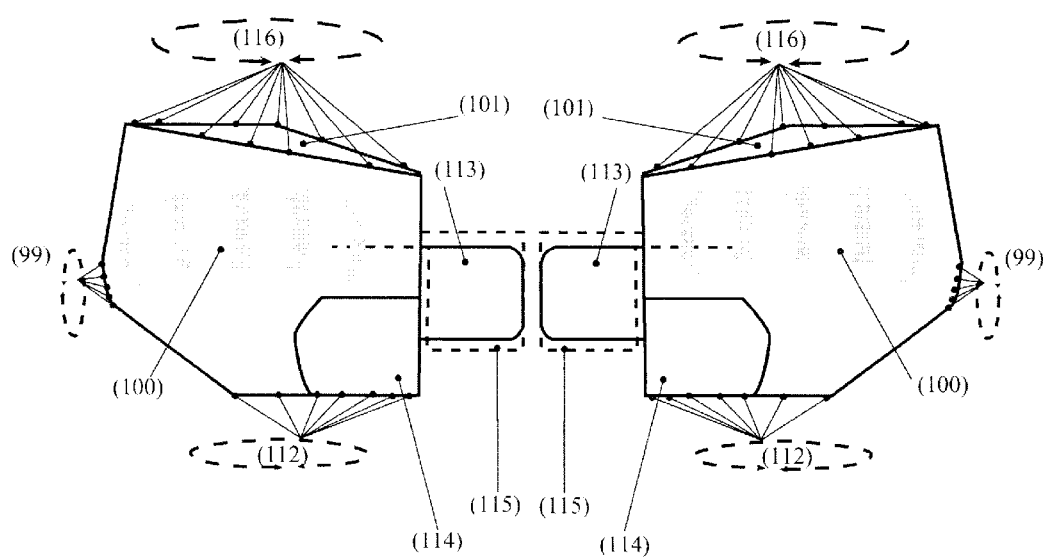
FIG. 5a shows a warmer for a hand (left hand, palm-side up) according to one example embodiment of the present invention.
FIG. 5b shows a warmer for a hand (right hand, palm-side up) according to one example embodiment of the present invention.

FIGS. 5a and 5b shows another example embodiment of the present invention for providing heat to the hand of a wearer, e.g., a warmer for a hand. This example embodiment is similar to the embodiment described above in connection with FIG. 1. FIG. 5a shows an example of a left hand design, palm side up; FIG. 5b shows a right hand, palm side up. In this embodiment, the fasteners 113 and 114 are hook and loop-type fasteners (e.g., Velcro). However, as described above, other types of fasteners are, of course, possible.

In the example embodiment of FIGS. 5a and 5b, a fastener 114 is positioned at one end of the base layer (see, e.g., FIG. 1) while the second end of the base layer includes a tab 115 with a fastener 113 (a mate to fastener 114). In the example embodiment, the tab 115 is situated for secure fit when the base layer is pulled around to the closure's mate 114. The tab 115 may or may not be of the same material as the base layer. FIGS. 5a and 5b also show the space provided for accommodating a hand. As shown, an opening 112 is provided for insertion of the hand. When the hand is inserted palm side up, the opening 112 will be occupied by the wearer's wrist. In the example embodiment of FIGS. 5a and 5b, the base layer includes an opening 99 for receiving the thumb of the wearer. The fingers of the wearer extend through opening 116. In one example embodiment of the present invention, the wearer's hand is inserted into opening 112 after the fasteners 113 and 114 are secured to one another. In another example embodiment, the base layer is wrapped around the wearer's hand (with the thumb extending through opening 99), and the fasteners 113 and 114 are then secured.

Figure 6A:
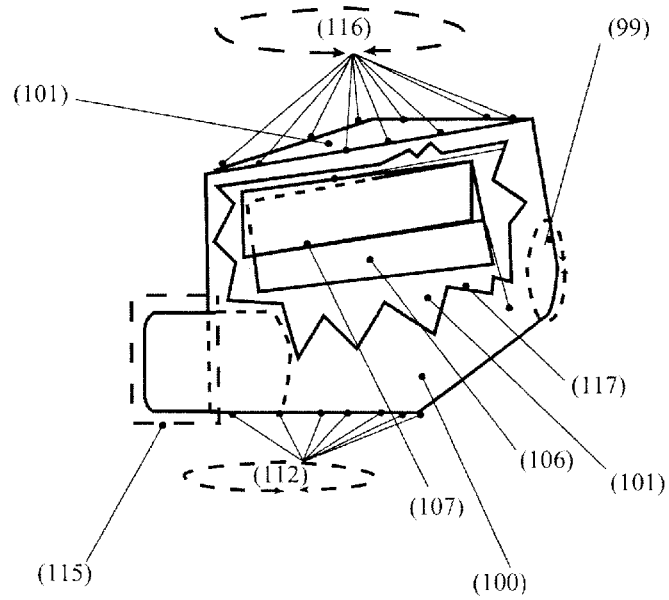
FIG. 6a shows a warmer for a hand (left hand, palm-side down) according to one example embodiment of the present invention.
Figure 6B:
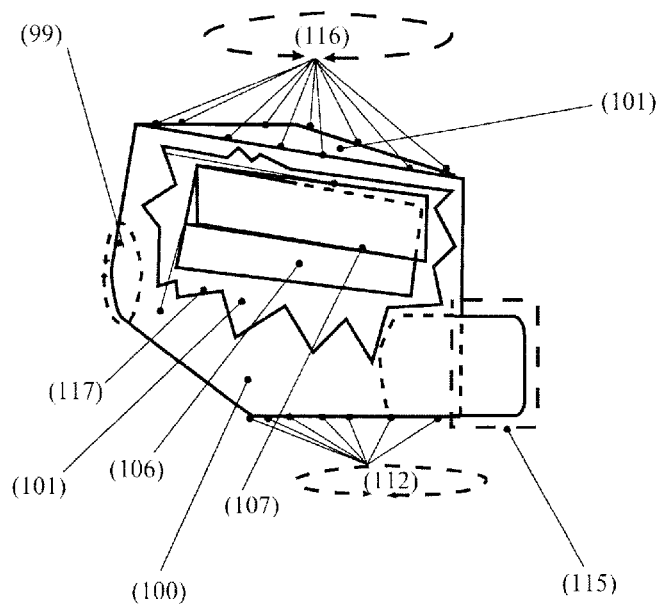
FIG. 6b shows a warmer for a hand (right hand, palm-side down) according to one example embodiment of the present invention.

FIGS. 6a and 6b show the example embodiments of FIGS. 5a and 5a (respectively), palmside down. These views also show an example of placement of pocket 106 in a breakaway view. The breakaway is represented by 117. The breakaway 117 is provided for ease of understanding of the example embodiment in order to show exemplary pocket placement. However, in this embodiment, the breakaway 117 is not part of the design. In this example embodiment, the pocket 106 is positioned so that when the heating device is inserted in the pocket 106, and the warmer for the hand is worn by the user the palm of the wearer is heated. In another embodiment, the pocket 106 is positioned so that the back of the hand of the wearer is heated.

Figure 7:
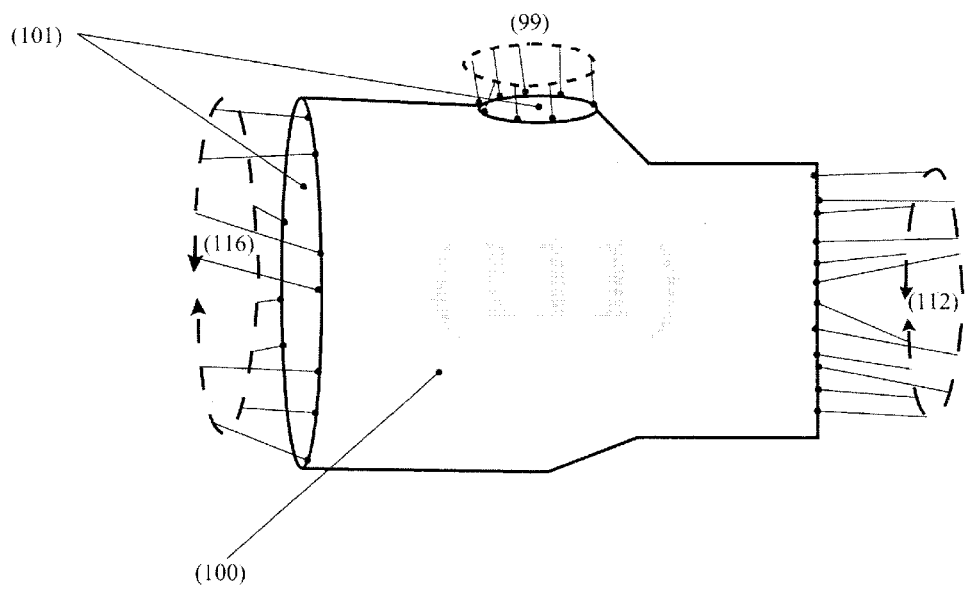
FIG. 7 shows a warmer for a hand (palm-side up) according to another example embodiment of the present invention.
Figure 8:
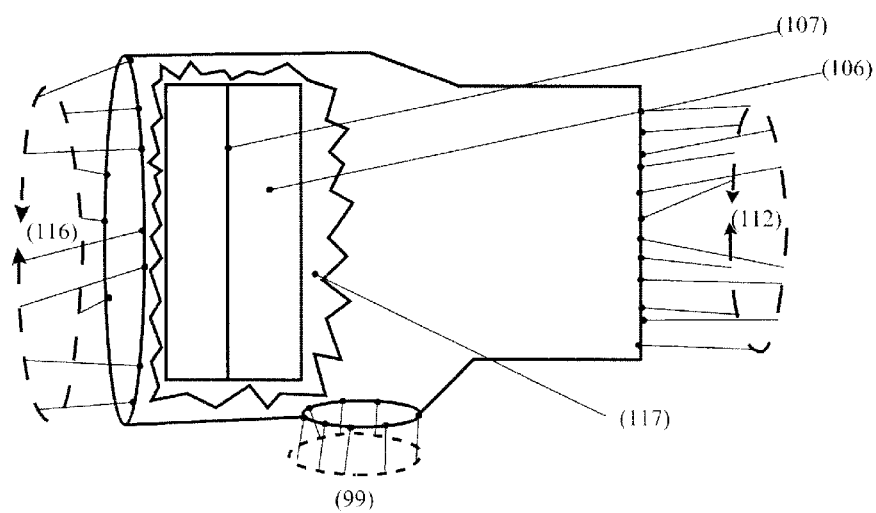
FIG. 8 shows another view of the warmer of FIG. 7 (palm-side down).

FIGS. 7 and 8 show a warmer for a hand according to another example embodiment of the present invention. FIG. 7 shows a view of the warmer, palm-side up. FIG. 8 shows a view of the warmer of FIG. 7, palm-side down. This embodiment is similar to that shown in FIGS. 6a and 6b, except that the warmer has a slip-on design. That is, the base layer is formed of one continuous piece (which may or may not have seams) and slips onto the hand of the wearer (via opening 112) like a glove. The embodiment of FIGS. 7 and 8 can be designed for the left and/or the right hand. In this embodiment, fasteners are not used.

Figure 9:
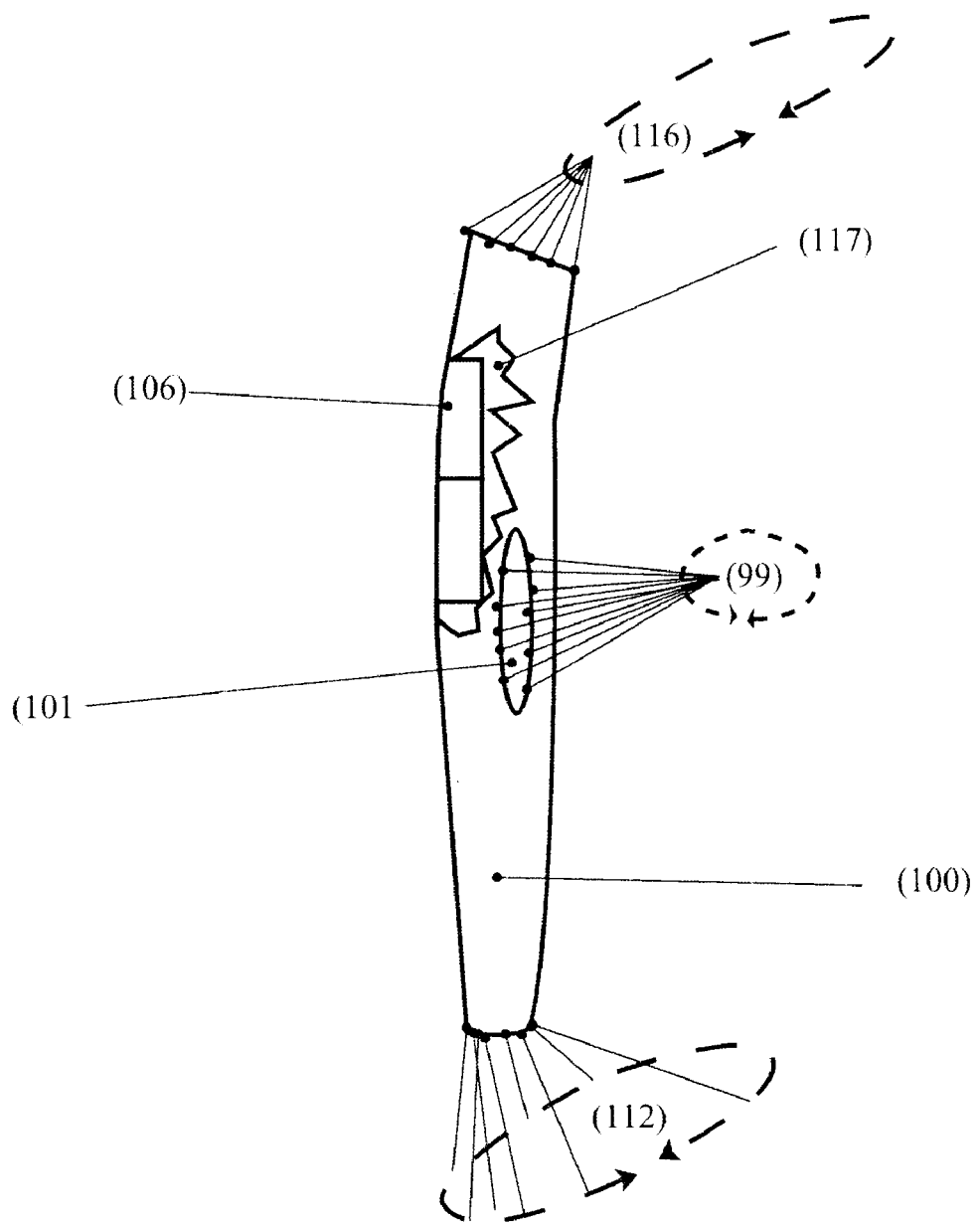
FIG. 9 shows a side view of the warmer of FIGS. 7 and 8.

FIG. 9 shows a side view of the embodiment illustrated in FIGS. 7 and 8. In this view, the opening 99 for the thumb is visible.

Figure 10:
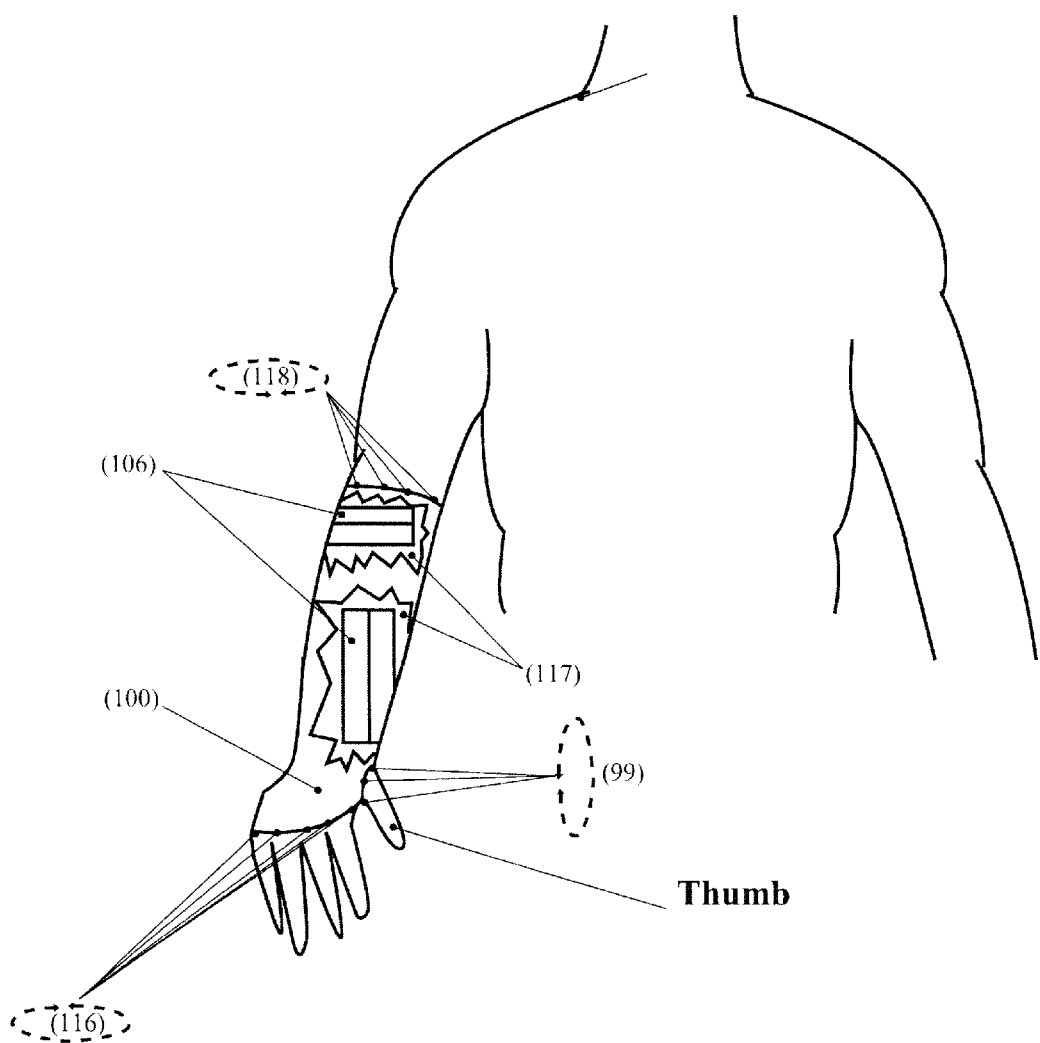
FIG. 10 shows an arm warmer, e.g., a warmer for the forearm of the wearer, according to one example embodiment of the present invention.

FIG. 10 shows an example arm warmer, e.g., a warmer for the lower arm of the wearer, according to one example embodiment of the present invention. The arm warmer illustrated is similar to that shown in FIGS. 7–9, e.g., it has a slip on design (that is, the wearer puts it on like a glove). In another embodiment, the arm warmer includes fasteners similar to those shown in FIGS. 6a and 6b.

In the embodiment shown in FIG. 10, one or more pockets 106 sized to removably receive heating devices are provided on the inside of the base layer. In this example, the base layer is sized to extend from the hand of the wearer to the elbow of the wearer. Like the embodiment of FIGS. 7–9, the base layer is provided with an opening 99 to receive the thumb of the wearer. The wearer's fingers extend through opening 116. In the arm warmer of FIG. 10, the arm of the wearer extends through an opening 118. In one example embodiment, it the base layer extends beyond the elbow of the user, the base layer may or may not include an opening for the elbow.

Figure 11:
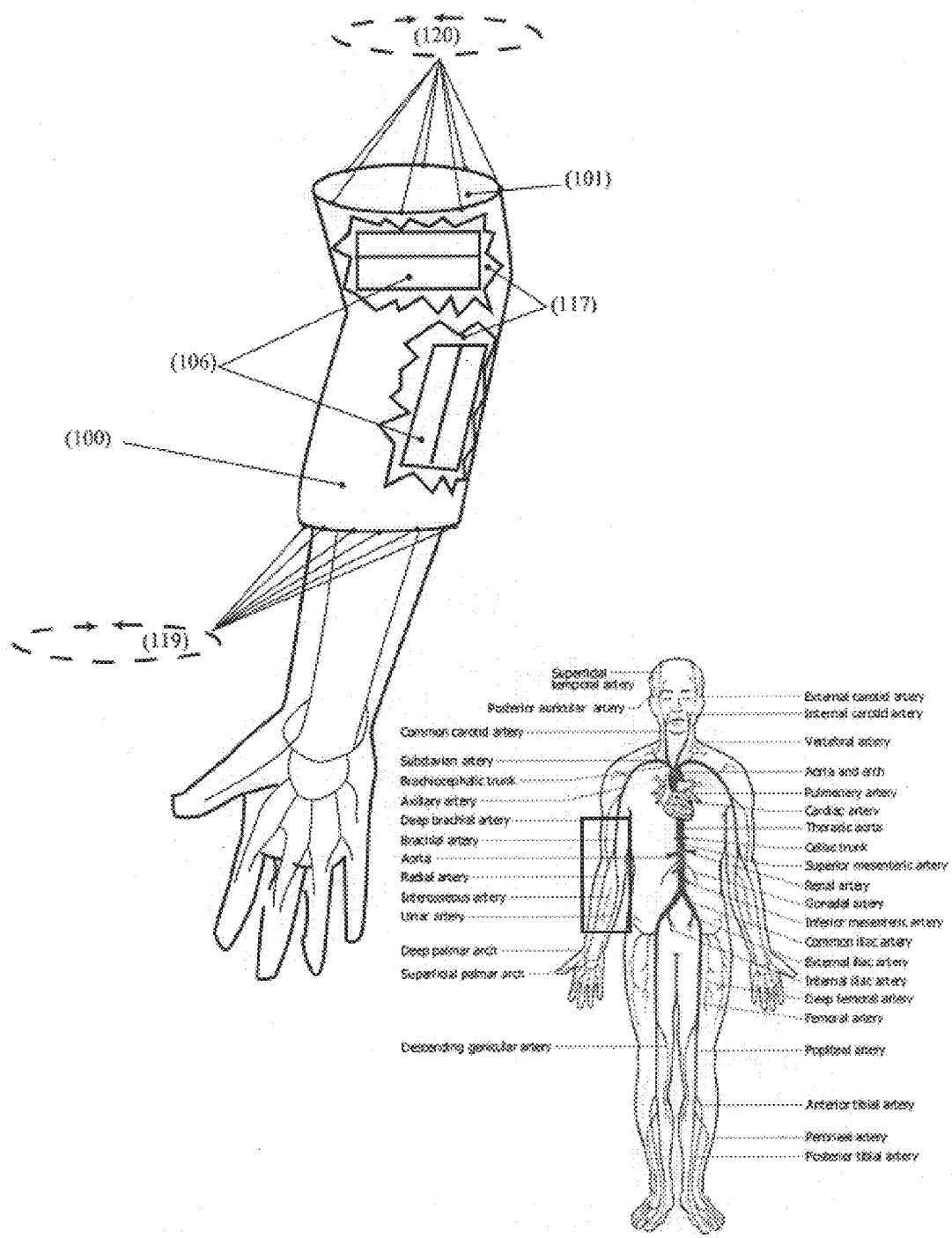
FIG. 11 shows an arm warmer, e.g., a warmer for the upper forearm and biceps area of the wearer, according to yet another example embodiment of the present invention.

FIG. 11 shows another example embodiment of the present invention. Here, a warmer for the upper forearm and the biceps area of the wearer is illustrated. In this embodiment, the base layer may or may not include an opening for the elbow.

The embodiment shown in FIG. 11 has a slip-on design. In particular, the base layer is formed of one piece (which may or may not have seams). The base layer includes one or more pockets 106 positioned to provide heat to the upper forearm and/or the biceps area of the wearer. In this embodiment, the wearer inserts a hand and arm into the opening 120. When this arm warmer is worn, the lower forearm, wrist and hand of the wearer extends through opening 119.

In another example embodiment, the arm warmer of FIG. 11 includes fasteners (similar to FIG. 1) for fastening ends of the base layer to each other. In this embodiment, the fasteners may be fastened first, and the wearer would then insert a hand and arm into the opening 120. Alternatively, the base layer may be wrapped around the upper forearm and biceps area of the wearer. The ends of the base layer could then be fastened together.

Figure 12:
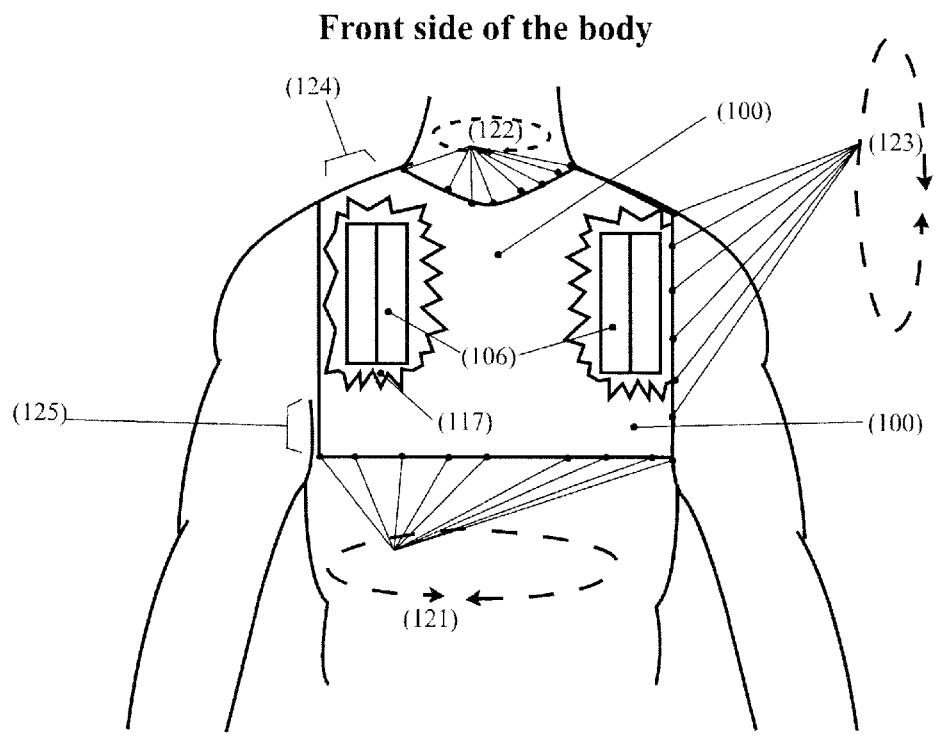
FIG. 12 shows a front view of a wanner for upper front and/or upper back of the arms of a wearer, according to one example embodiment of the present invention.
Figure 13:
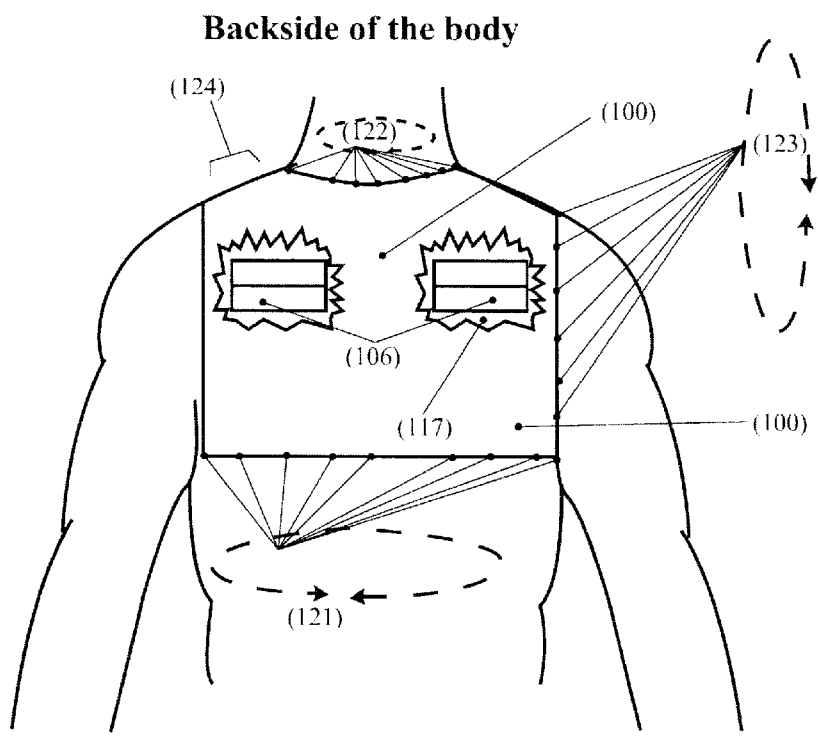
FIG. 13 shows a rear view of the warmer of FIG. 12.

FIGS. 12 and 13 show different view of a warmer for the upper front and/or upper back of the arms of a wearer according to an example embodiment of the present invention. In particular, FIG. 12 shows a front view while FIG. 13 shows a rear view. In accordance with this embodiment, one or more pockets 106 may be included on the base layer on both the front portion and the back portion. In alternate embodiments, pocket(s) 106 may be provided on only the front portion or only the back portion.

In the example embodiment, the base layer may be formed into a vest-type garment (which may or may not include seams, and may or may not include fasteners). In particular, the base layer 100 is sized to fit the circumference of the upper torso. The opening 121 is the entrance point for the head, shoulders, arms and torso to pass through so that the space 111 is occupied by the user. The head is extended through the space 111 and extends through opening 122. The arms and shoulders extent through opening 121 and through space 111, with the arms extending through openings 123.

In the example embodiment sown in FIGS. 12 and 13, the front of the garment is connected to the back of the garment at the shoulders 124 and under each arm at 125 via, for example, fasteners, seams, etc. Alternatively, the front and back of the garment may be formed from a single piece of material without seams, with openings 122 and 121 being provided. In yet another embodiment, the front and back of the garment are connected only at the shoulders; thus the front and the back of the garment are in the form of flaps. In yet another embodiment of the invention, the front and back of the garment are formed from a single flat piece of material with an opening 122 being provided. In this embodiment, the front and the back of the garment are in the form of flaps.

Figure 14:
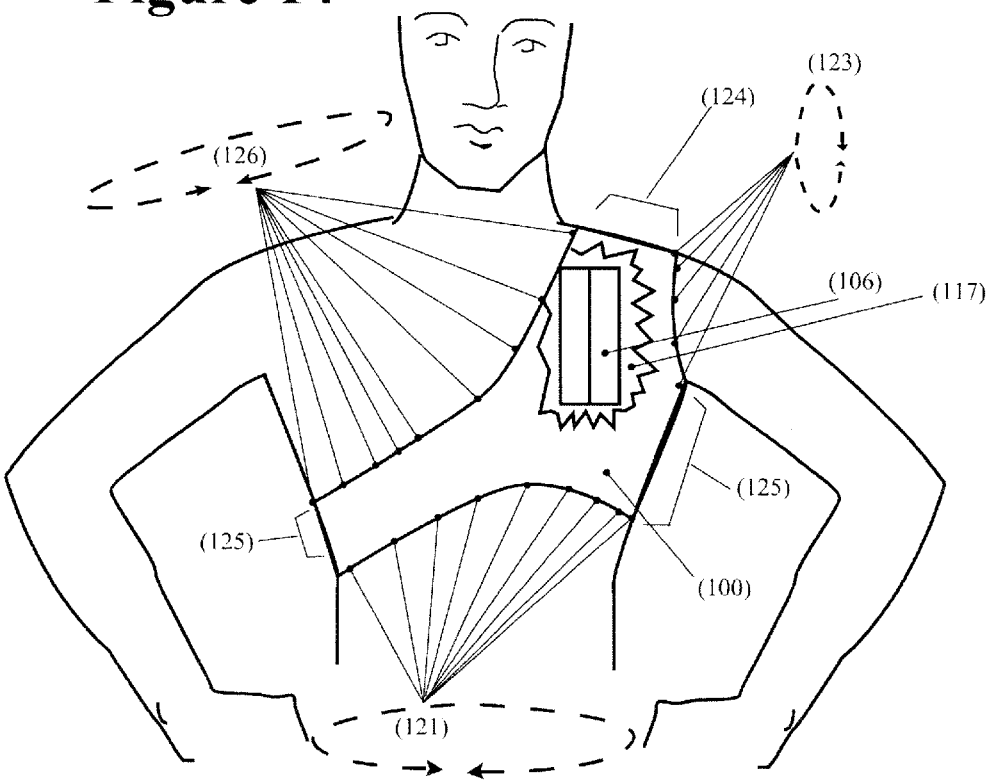
FIG. 14 shows a front view of a warmer for a left shoulder area of a wearer, according to one example embodiment of the present invention.
Figure 15:
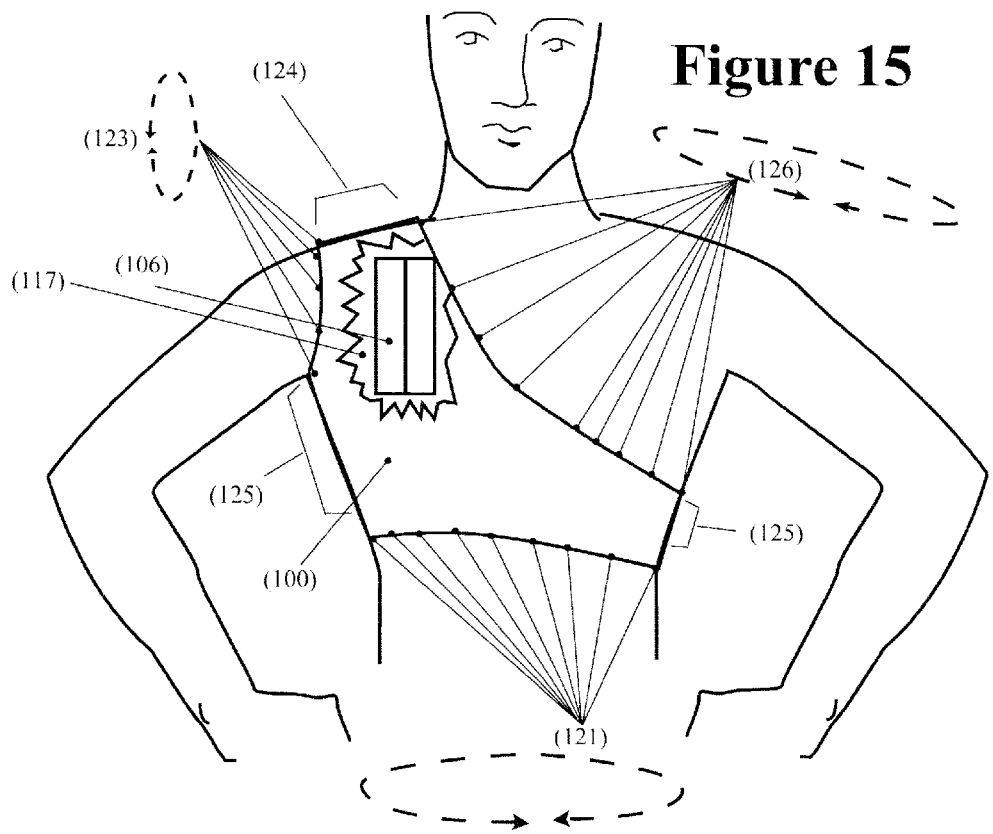
FIG. 15 shows a front view of a warmer for a right shoulder area of a wearer, according to one example embodiment of the present invention.

FIGS. 14 and 15 show yet another example embodiment of the present invention for warming the shoulder areas of a wearer. More specifically, FIG. 14 shows a warmer for a right shoulder, and FIG. 15 shows a warmer for a left shoulder. In this example embodiment, the warmer is in the form of a sling. As shown in the figures, an opening 126 is provided to accommodate the wearers head and the shoulder opposite to the shoulder being warmed. In this example embodiment, the base layer extends from the shoulder being warmed, diagonally across the wearer's chest and to the wearer's waist. At points 124 and 125, the front of the warmer is either connected to (via, for example, fasteners or seams) to the back of the garment, or is in one piece with the back of the warmer at those points.

In the example embodiments shown in FIGS. 14 and 15, at least one pocket 106 is provided on the inside portion of the base layer. The pocket(s) 106 may be arranged so that heat may be applied to either the front of the shoulder, the back of the shoulder, or both.

Figure 16:
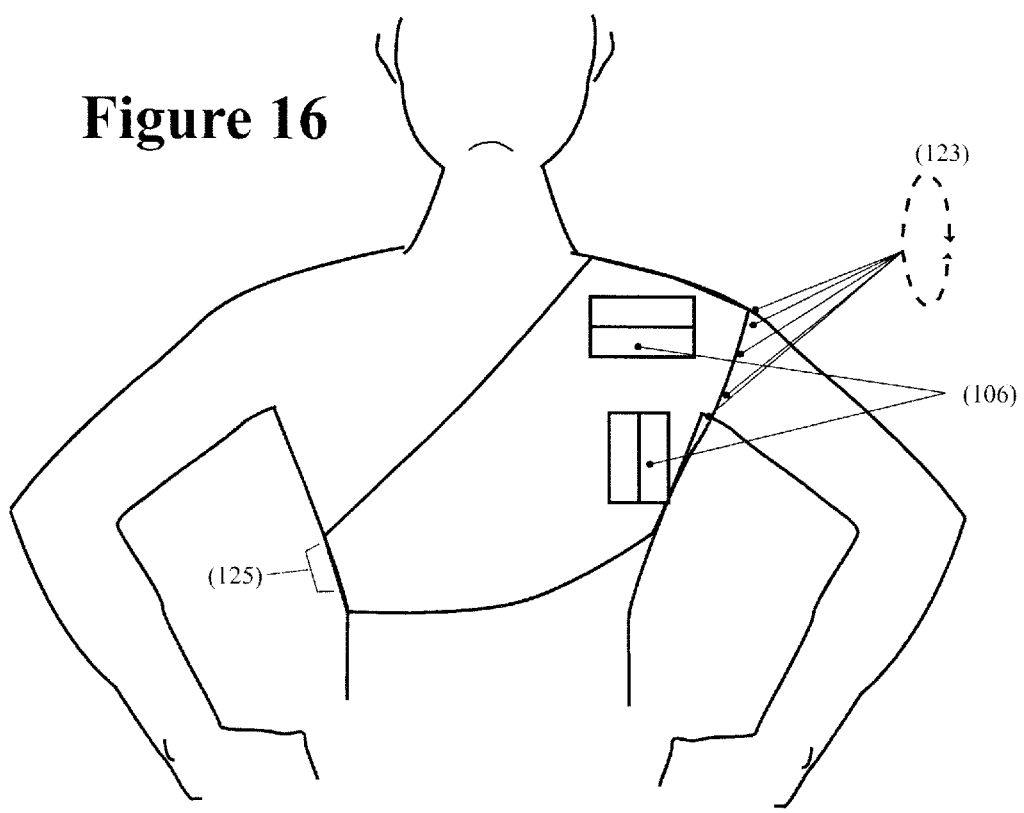
FIG. 16 shows a rear transparent view of the warmer of FIG. 15.
Figure 17:
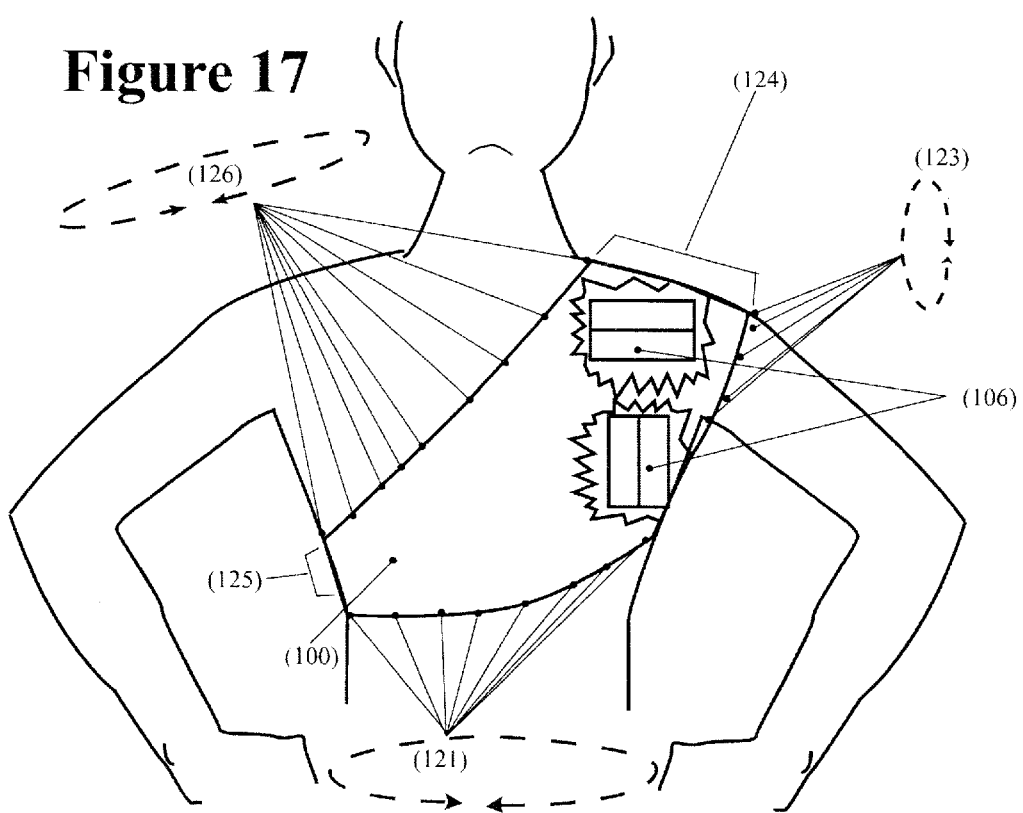
FIG. 17 shows a rear "breakaway" view of the warmer of FIG. 15.

FIG. 16 is a rear transparent view of the warmer of FIG. 15. In this figure, example placement of pockets 106 are shown. FIG. 17 is another view of the rear of the warmer of FIG. 15.

FIGS. 18 and 19 shows an example of a warmer configured to warm the lower torso/trunk of the wearer, according to one example embodiment of the present invention. In this A example embodiment, the warmer has a slip-on design. However, as described above, the warmer design is shown as a slip on style, although as mentioned in connection with example embodiments discussed above, the warmer may include, for example, fasteners.

In the example embodiment of FIGS. 18 and 19, a wearer inserts the wearer's legs and lower torso/trunk in through opening 127. Openings 128 are provided to accommodate the legs of the wearer. In this embodiment, at least one pocket 106 is provided. The pockets are positioned so that when the warmer is worn, the upper area of the wear's legs are warmed.

FIGS. 20 and 21 show a warmer for an area near the knee of a wearer according to one example embodiment of the present invention. In this embodiment, the base layer is in the form of a sleeve which may be slipped onto the leg of the wearer and positioned over the knee and area surrounding the knee 132 of the wearer. Although in this embodiment, the base layer is shown as a single piece of material, as described above in connection with other embodiments, the base layer may also include fasteners to secure two ends of the base layer together.

As shown in FIGS. 20 and 21, the warmer includes at least one pocket configured to receive a heating device. The base layer is configured with an opening 130 through which the wearer inserts a foot and leg, and an opening 131 through which the wearer's foot and lower leg extends. As shown in FIGS. 20 and 21, when the warmer is worn, heat supplied by the heating device is applied to the area surrounding the knee of the wearer.

FIGS. 22 and 23 show another warmer for warming the area around the knee of a wearer, according to another example embodiment of the present invention. This embodiment is similar to that shown in FIGS. 22 and 23, except the embodiment of FIGS. 22 and 23 includes an opening 133 for the knee area or patella.

In FIG. 23, 134 represents a different orientation of pocket(s) 106, similar to pocket(s) 106 shown in FIG. 21.

Figure 25:
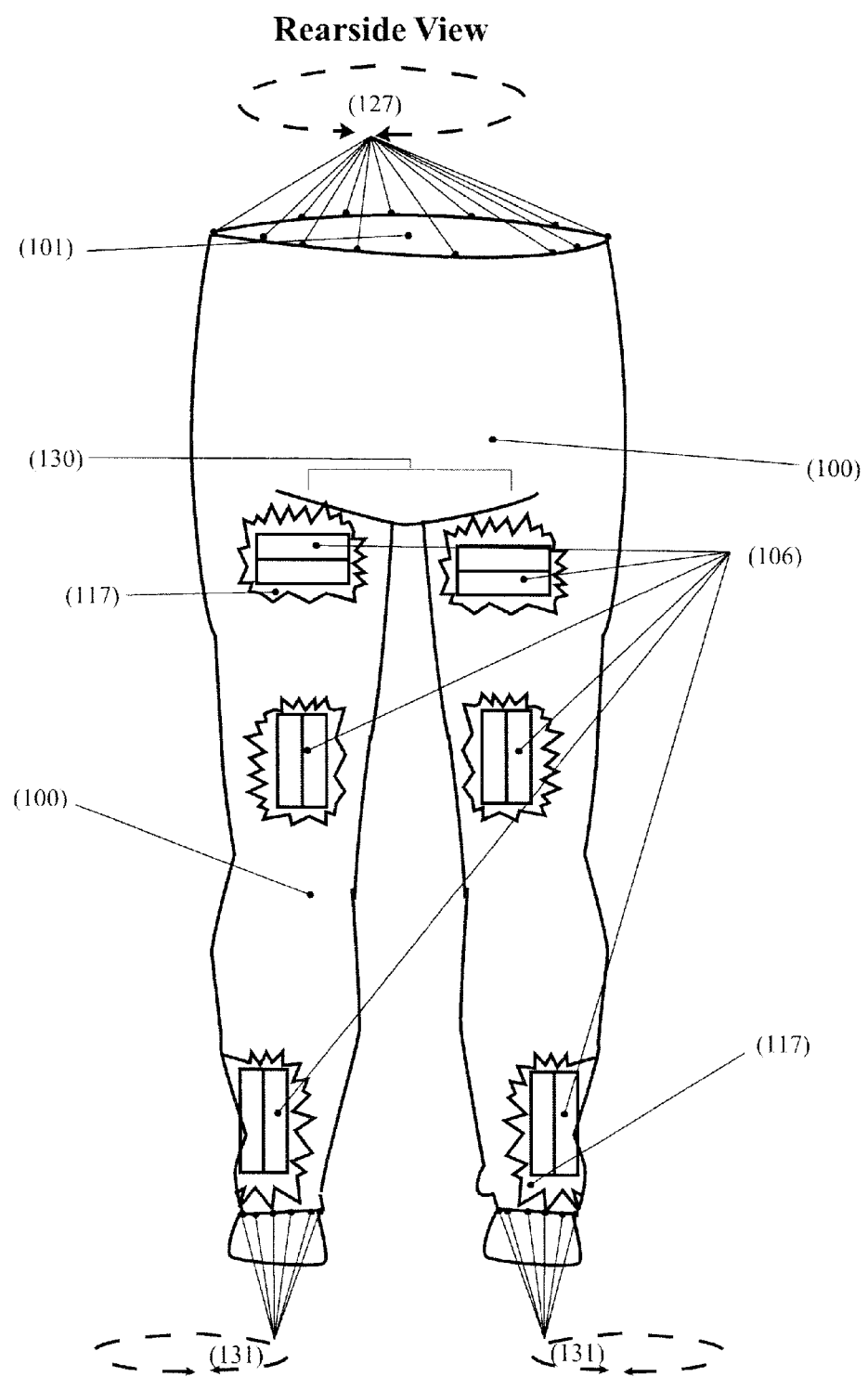
FIG. 25 shows a rear view of the warmer of FIG. 24.

FIGS. 24 and 25 show a warmer for the legs of the wearer, according to one example embodiment of the present invention. In this example embodiment, the base layer is configured in the form of leggings. The base layer includes an opening 127 for receiving the wearer's legs and lower trunk. The wearer's feet extend through openings 131. In this embodiment, at least one pocket 106 is provided on the base layer. The pockets 106 are positioned on the base layer to provide heat to portions of the legs of the wearer.

In the example embodiment, the base layer has a one-piece slip-on design. In other embodiments, fasteners may be provided, e.g., at the waist area.

Figure 26:
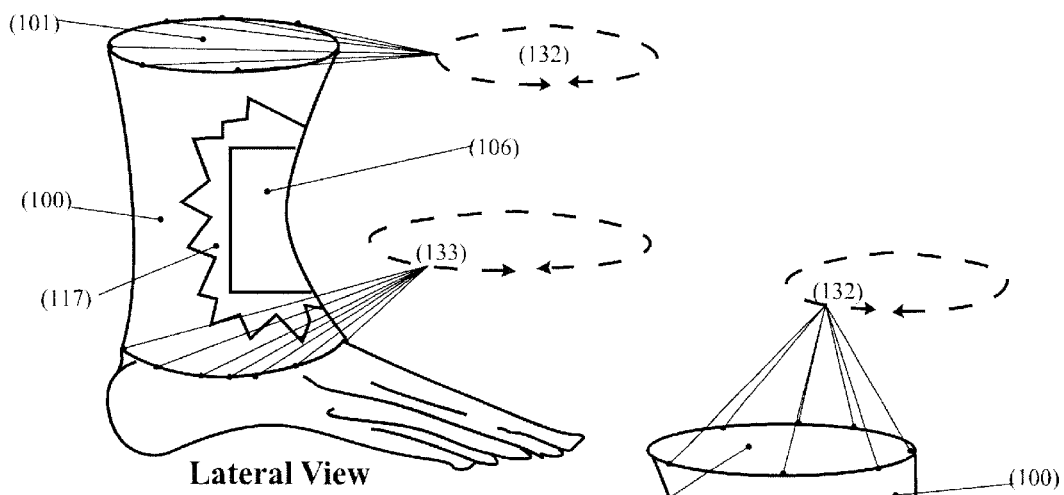
FIG. 26 shows a lateral view of a warmer for the lower extremities of the wearer, according to one example embodiment of the present invention.
Figure 27:
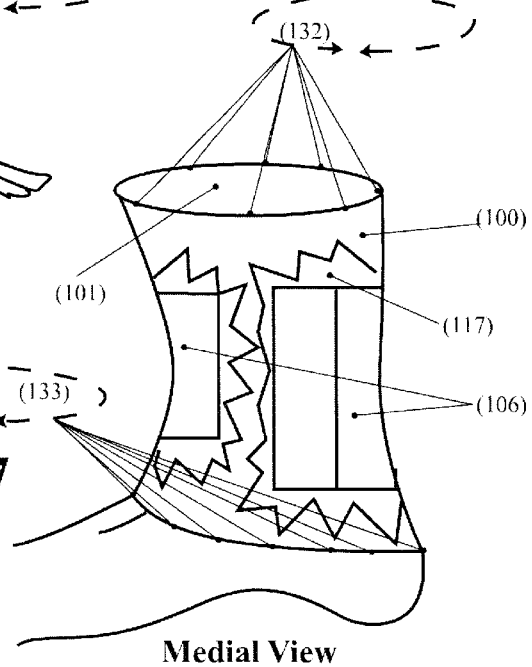
FIG. 27 shows a medial view of the warmer of FIG. 26.
Figure 28:
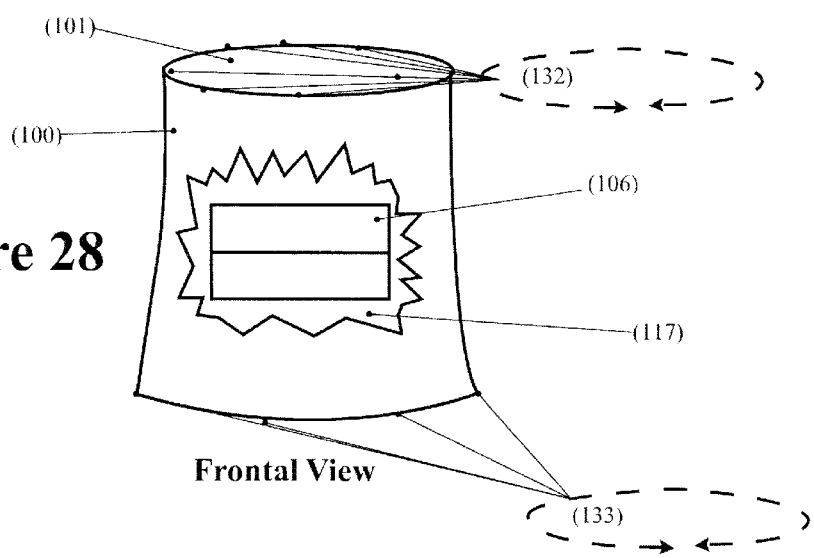
FIG. 28 shows a front view of the warmer of FIG. 26.

FIGS. 26–28 show a warmer for the lower extremities, e.g., ankle area of the wearer, according to one example embodiment of the present invention. In this embodiment, the base layer is configured to accommodate a lower extremity of the wearer, here, the ankle area. The base layer includes an opening 132 for receiving the foot and ankle area of the wearer. The wearer's foot extends through another opening 133. The base layer is provided with one or more pockets 106, each pocket 106 being configured to receive a heating device. The pockets 106 are positioned to warm the lower extremity (e.g., ankle area) of the wearer.

Figure 29:
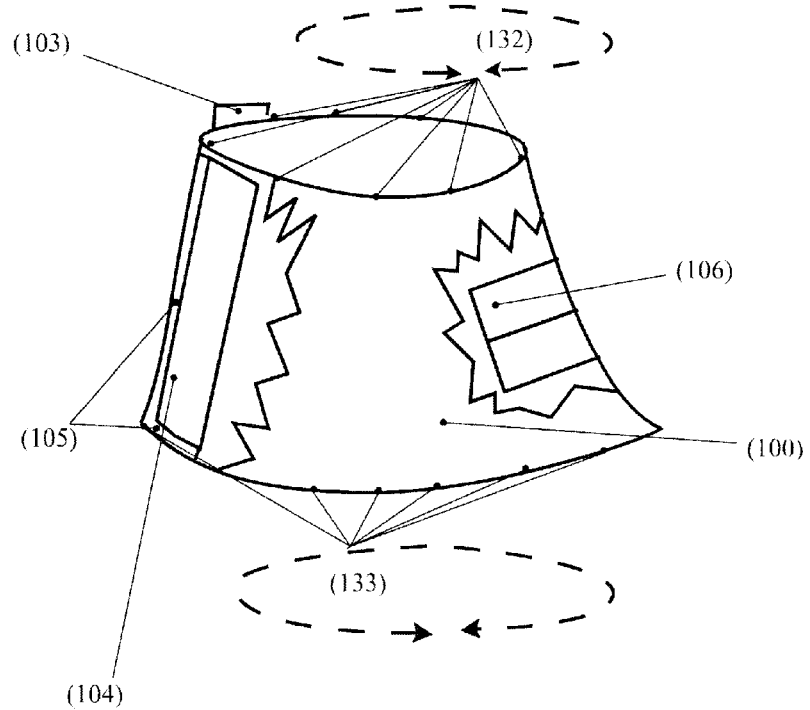
FIG. 29 shows a view of a warmer for the lower extremity of the wearer, according to another example embodiment of the present invention.
Figure 30:
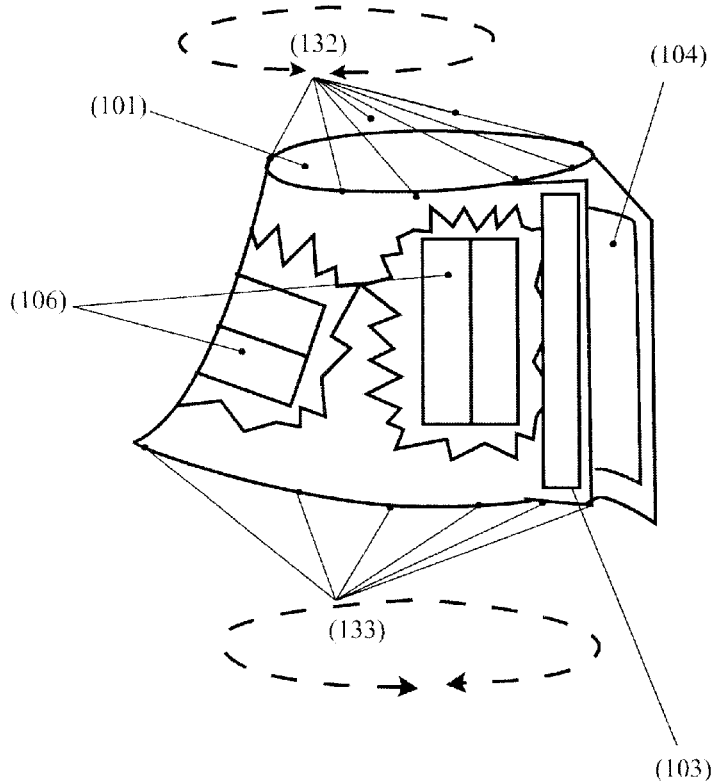
FIG. 30 shows another view of the warmer of FIG. 29.

In the embodiment shown in FIGS. 26–28, the base layer is configured as a cuff (which may or may not have seams). In other embodiments, the base layer may also include fasteners for fastening ends of the base layer together so that the base layer surrounds the lower extremity of the wearer. FIGS. 29 and 30 show one such example embodiment. In this embodiment, the base layer may be wrapped around the ankle area of the wearer. Ends of the base layer are fastened together using fasteners 103 and 104.

Figure 31:
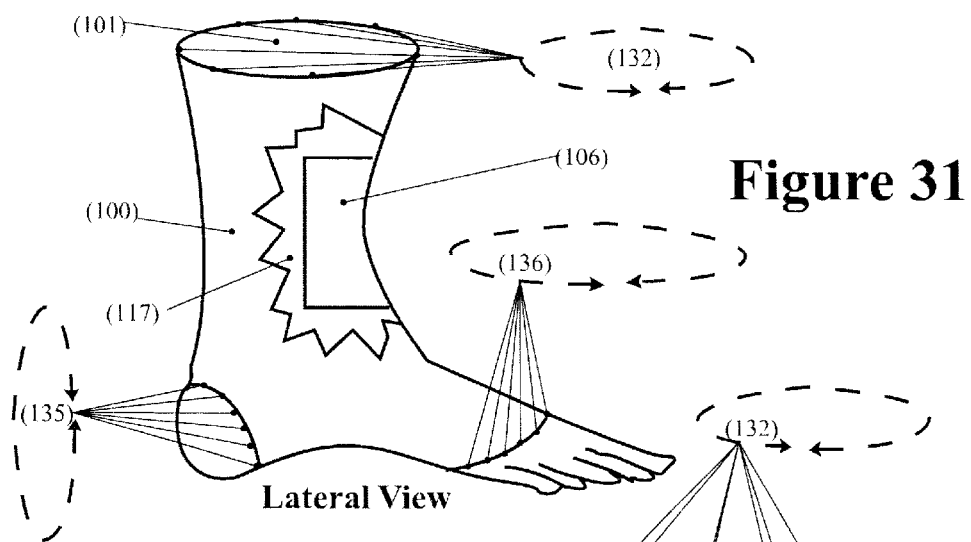
FIG. 31 shows a lateral view of another warmer for the lower extremity of the wearer, according to yet another example embodiment of the present invention.
Figure 32:
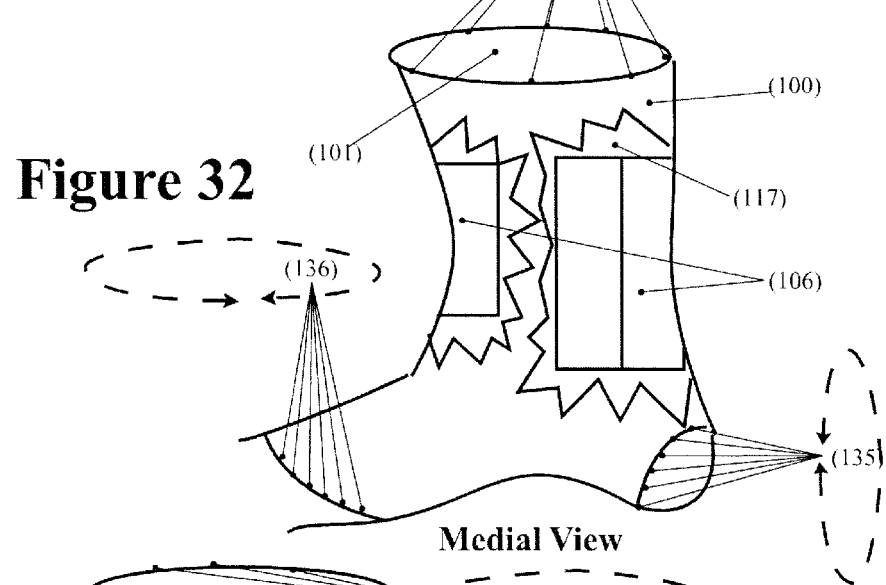
FIG. 32 shows a medial view of the warmer of FIG. 31.
Figure 33:
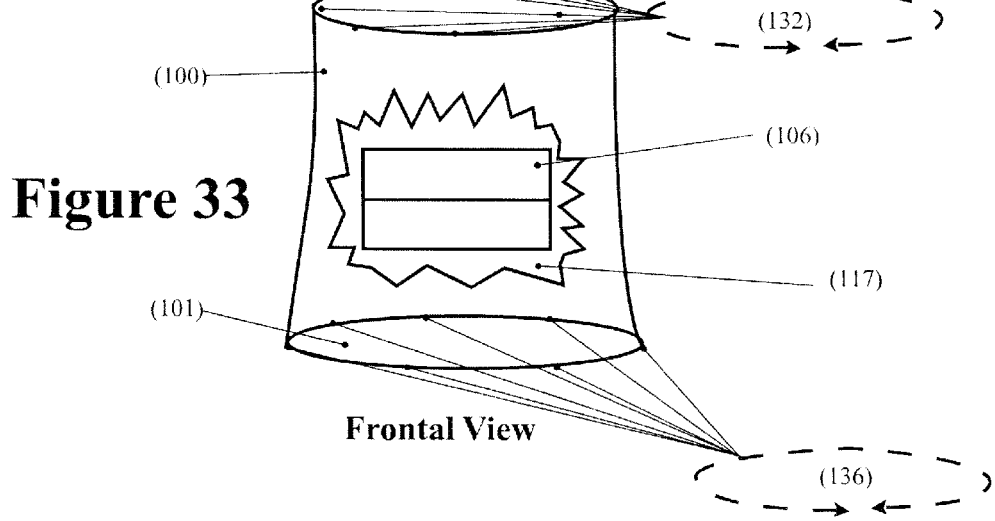
FIG. 33 shows a front view of the warmer of FIG. 31.

FIGS. 31–33 show another example embodiment of the present invention. In particular, FIGS. 31–33 show a warmer similar to that shown in FIGS. 26–28. In this embodiment, the base layer also includes a portion 100 for accommodating the foot of the wearer. The wearer's toes extend through opening 136, while the wearer's heal extends through opening 135.

In accordance with the example embodiments, the base layer may be configured as, for example, a garment, an undergarment or a garment liner.

While the Figures show the above example embodiment for a human wearer, the embodiments may also be configured to warm an appendage of a non-human animal.

What is claimed is:

1. A body fitting garment, said garment having an open end for receiving a body portion of a wearer and a second open end for a portion of that body portion to pass through comprising:
    a base layer including a pocket, the base layer configured to accommodate the appendage of the wearer, the pocket configured for removable insertion of the heating device so that when the heating device is inserted in the pocket and the device is worn by the wearer, heat from the heating device is applied to the appendage.
    wherein the body garment covers a major muscle group of the body portion.

2. The device according to claim 1, wherein the base layer has a first end and a second end, the device further comprising:
    a fastener configured to fasten the first end of the base layer to the second end of the base layer.

3. The device according to claim 1, wherein the base layer is a continuous cuff of material.

4. The device according to claim 1, wherein the heating device is an air activated heating device.

5. The device according to claim 1, wherein the heating device is composed of iron powder.

6. The device according to claim 1, wherein the heating device is an air activated heating device.

7. A The device according to claim 1, wherein the base layer is configured to accommodate a wrist of the wearer, and wherein when the heating device is inserted in the pocket and the device is worn by the wearer, heat from the heating device is applied to the wrist.

8. The device according to claim 1, wherein the base layer is configured to accommodate a hand of the wearer, and wherein when the heating device is inserted in the pocket and the device is worn by the wearer, heat from the heating device is applied to the hand.

9. The device according to claim 1, wherein the base layer is configured to accommodate a leg of the wearer, and wherein when the heating device is inserted in the pocket and the device is worn by the wearer, heat from the heating device is applied to the leg.

10. The device according to claim 1, wherein the base layer is configured to accommodate a arm of the wearer, and wherein when the heating device is inserted in the pocket and the device is worn by the wearer, heat from the heating device is applied to the arm.

11. The device according to claim 1, wherein the pocket has an opening configured to receive the heating device, the opening being on an inside portion of the base layer, the inside portion of the base layer being a side of the base layer which, when the device is worn by the wearer, faces the wearer.

12. The device according to claim 1, wherein the base layer is configured to accommodate an appendage of a non-human animal.

13. A method for applying heat from a heating device to a body portion of a wearer comprising:
    providing a body fitting garment having an open end for receiving a body portion of a wearer and a second open end for a portion of that body portion to pass through;
    providing a base layer including a pocket configured to accommodate a body portion of the wearer;
    removably inserting said heating device in said pocket;
    wrapping the base layer around a major muscle group of the body portion so that heat from the heating device is applied to said body portion.

14. The method according to claim 13, wherein the wrapping step includes wrapping the base layer around a wrist of the wearer.

15. The method according to claim 13, wherein the wrapping step includes wrapping the base layer around a hand of the wearer.

16. The method according to claim 13, wherein the wrapping step includes wrapping the base layer around an arm of the wearer.

17. The method according to claim 13, wherein the wrapping step includes wrapping the base layer around an appendage of a non-human animal.

18. The method according to claim 13, further comprising:
    providing the pocket with an opening that faces the wearer when the base layer is worn by the wearer.

19. The method according to claim 13, wherein the removably inserting step includes removably inserting an iron powder heating device.

20. The method according to claim 13, wherein the removably inserting step includes removably inserting an air activated heating device.

21. A method for applying heat from a heating device to a body portion of a wearer, comprising:
    providing a body fitting garment having an open end for receiving a body portion of a wearer and a second open end for a portion of that body portion to pass through;
    providing a base layer having a pocket, the pocket sized to accommodate the heating device, the base layer configured to accommodate the appendage of the wearer;

removably inserting the heating device in the pocket of the base layer; and receiving in the base layer the appendage so that heat from the heating device is applied to the appendage of the wearer.

22. The method according to claim 21, wherein the receiving step includes receiving in the base layer a wrist of the wearer.

23. The method according to claim 21, wherein the receiving step includes receiving in the base layer a hand of the wearer.

24. The method according to claim 21, wherein the receiving step includes receiving in the base layer an arm of the wearer.

25. The method according to claim 21, further comprising:

providing the pocket with an opening that faces the wearer when the base layer is worn by the wearer.

26. The method according to claim 21, wherein the receiving step includes receiving in the base layer an appendage of a non-human animal.

27. The method according to claim 21, wherein the removably inserting step includes removably inserting an iron powder heating device in the pocket of the base layer.

28. The method according to claim 21, wherein the removably inserting step includes removably inserting an air activated heated device in the pocket of the base layer.

* * * * *

UNITED STATES PATENT AND TRADEMARK OFFICE
CERTIFICATE OF CORRECTION

| | | |
|---|---|---|
| PATENT NO. | : 6,598,235 B2 | Page 1 of 1 |
| APPLICATION NO. | : 09/921284 | |
| DATED | : July 29, 2003 | |
| INVENTOR(S) | : Athalene April Bulla | |

It is certified that error appears in the above-identified patent and that said Letters Patent is hereby corrected as shown below:

In column 7, line 47, delete "insertion of the" and replace with -- insertion of a --

In column 8, line 34, delete "inserting said heating" and replace with -- inserting a heating --

In column 8, line 65, delete "the heating device" and replace with -- a heating device --

Signed and Sealed this
Twenty-third Day of August, 2011

David J. Kappos
*Director of the United States Patent and Trademark Office*